(12) United States Patent
Clabaugh et al.

(10) Patent No.: US 10,294,168 B2
(45) Date of Patent: May 21, 2019

(54) METHOD OF PRODUCING FERTILIZER FROM ALCOHOLIC FERMENTATION WASTE

(71) Applicants: Christopher Clabaugh, Grass Valley, CA (US); Beau Ulrich, Meadow Vista, CA (US)

(72) Inventors: Christopher Clabaugh, Grass Valley, CA (US); Beau Ulrich, Meadow Vista, CA (US)

( * ) Notice: Subject to any disclaimer, the term of this patent is extended or adjusted under 35 U.S.C. 154(b) by 126 days.

(21) Appl. No.: 15/494,388

(22) Filed: Apr. 21, 2017

(65) Prior Publication Data

US 2017/0305801 A1    Oct. 26, 2017

Related U.S. Application Data

(60) Provisional application No. 62/326,324, filed on Apr. 22, 2016.

(51) Int. Cl.

| | | |
|---|---|---|
| *C07C 29/80* | (2006.01) | |
| *C05F 5/00* | (2006.01) | |
| *C05G 3/00* | (2006.01) | |
| *C05B 17/00* | (2006.01) | |
| *C05C 11/00* | (2006.01) | |
| *C05D 1/00* | (2006.01) | |
| *C05D 3/00* | (2006.01) | |
| *C05D 5/00* | (2006.01) | |
| *C05D 9/02* | (2006.01) | |

(52) U.S. Cl.
CPC .............. *C05F 5/006* (2013.01); *C05B 17/00* (2013.01); *C05C 11/00* (2013.01); *C05D 1/00* (2013.01); *C05D 3/00* (2013.01); *C05D 5/00* (2013.01); *C05D 9/02* (2013.01); *C05F 5/008* (2013.01); *C05G 3/00* (2013.01); *C05G 3/0064* (2013.01); *C07C 29/80* (2013.01)

(58) Field of Classification Search
None
See application file for complete search history.

(56) References Cited

U.S. PATENT DOCUMENTS 5,981,441 A  *  11/1999  Rodder .................... A01G 7/06
                                                        504/353
2008/0173052 A1 *  7/2008  Takamiya ............... C02F 1/441
                                                         71/26
(Continued)

FOREIGN PATENT DOCUMENTS

JP            2-275791    * 11/1990

*Primary Examiner* — Wayne A Langel (57) ABSTRACT

The invention relates to a method of producing a fertilizer composition from a feedstock that includes alcoholic beverages, waste product derived from the production of alcoholic beverages, or mixtures of the same. The feedstock is subjected to distillation to remove most of the ethanol and pH adjustment using a base. The invention also relates to a method of imparting flavor to a plant starting with the same feedstock, subjecting the feedstock to distillation and pH adjustment, and adding a flavorant to the resultant liquid before fertilizing the plant. The invention also relates to a method of producing a solid or liquid and solid foodstuff suitable for fish, bovine, swine, and the like for increasing dietary efficiency and reducing environmentally harmful solid and gaseous output.

26 Claims, 8 Drawing Sheets

Plant treated with fertilizer of the invention (56) References Cited

U.S. PATENT DOCUMENTS

| | | | | |
|---|---|---|---|---|
| 2009/0298690 | A1* | 12/2009 | Navalpotro | C05D 9/00 504/117 |
| 2011/0113843 | A1* | 5/2011 | Mantelatto | C05F 5/00 71/23 |
| 2013/0312471 | A1* | 11/2013 | Martinez Garmendia | C05F 5/008 71/23 |
| 2014/0051574 | A1* | 2/2014 | Riebel | A01N 65/44 504/101 |

* cited by examiner

FIG. 1A  FIG. 1B  FIG. 1C

Plant #1 (Water only)  Plant #2 (Fertilizer of the invention)  Plant #3 (Guano based fertilizer)

From left to right: Plant #1 (Water only), Plant #2 (Fertilizer of the invention), Plant #3 (Guano based fertilizer)

FIG. 1D

From left to right: Plant #1 (Water only), Plant #2 (Fertilizer of the invention), Plant #3 (Guano based fertilizer)

FIG. 2A

FIG. 2B — Plant treated with fertilizer of the invention

FIG. 3A Plant treated with water only

FIG. 3B Plant treated with Guano

FIG. 3C Plant treated with fertilizer of the invention

FIG. 4B Plant treated with fertilizer of the invention

FIG. 4A Plant treated with water only

FIG. 5B
Plant treated with fertilizer of the invention

FIG. 5A
Plant treated with water only

FIG. 6B Plant treated with fertilizer of the invention

FIG. 6A Plant treated with water only

METHOD OF PRODUCING FERTILIZER FROM ALCOHOLIC FERMENTATION WASTE

This patent application claims priority under 35 U.S.C. § 119(e) from U.S. provisional patent application Ser. No. 62/326,324, filed Apr. 22, 2016, entitled Method for Producing Fertilizer from Alcoholic Fermentation Waste

FIELD OF THE INVENTION

The invention relates to a method of producing a fertilizer from a feedstock that includes alcoholic beverages, waste product derived from the production of alcoholic beverages, and mixtures of the same. The invention also relates to a method of imparting flavor to a plant that may include starting with the aforementioned feedstock, subjecting the feedstock to distillation and pH adjustment, and adding a flavorant to the resultant liquid before fertilizing the plant.

BACKGROUND OF THE INVENTION

Alcohol production using the process of fermentation is practiced throughout the United States and in most of the world. Agricultural products like grapes, sugar cane, sugar beet, and different grains and cereals are either fermented directly or fermented after various sub-processing steps. Whether the resultant alcohol is undistilled (e.g., wine, beer) or distilled (e.g., brandy), the process produces a variety of waste streams. Examples include but are not limited to discarded fruit, discarded lees from wine production, grape pomace, and still bottoms.

In some circumstances, the alcohol beverage itself may become a waste stream. For example, if the wine does not meet quality control standards, it may have no marketable value and thus require disposal. In such circumstances, a once valued product may become a costly burden to the producer.

No standard method exists for handling the waste streams noted above. Some of the waste streams (particularly, the solid waste streams like pomace) are placed in a landfill or composted. Other waste streams leak into the ground on site or are directed to a municipal or industrial sewage system. Such disposal options become a cost and environmental burden.

Thus, there is a real need to eliminate disposal of large quantities of waste streams generated from alcohol production. Accordingly, the principal object of the invention is to provide methods to treat waste streams generated from alcohol production in order to derive value from these waste streams. Another object of the invention is to provide methods to produce both an alcoholic beverage and a fertilizer as part of the same process. Other objects will also be apparent from the following description of the invention.

SUMMARY OF THE INVENTION

In order to realize the object of the invention, the present inventors have discovered a cost effective method for using the waste streams from alcohol production to produce a useful fertilizer. The methods of the invention eliminate the need for large scale disposal of the waste streams and provide for the recovery of valuable components there from. The fertilizer has proven to be effective at enhancing the growth of a variety of plants.

Broadly stated, the objects of the invention are realized, according to one aspect of the invention, by producing a fertilizer or a foodstuff from a waste alcoholic beverage.

More specially, the method of producing a fertilizer from an alcoholic beverage comprises: (a) subjecting the alcoholic beverage to distillation to produce a liquid at the bottom of a still with an alcohol concentration of between about 0.05% by volume and 0.25% by volume, preferably from about 0.005% by volume to 0.25% by volume, and (b) adjusting the pH of the liquid to a range of 5.5-6.5 using a base to produce a fertilizer. In many embodiments, the fertilizer is a liquid.

The plant fertilizer of the invention comprises a liquid or liquid/solid mixture of waste product from the production of an alcoholic beverage, the waste product having an alcohol concentration of about 0.05% by volume of said waste product to about 0.25% by volume of said waste product; preferably from 0.005% by volume to 0.25% by volume; no more than 1% ethanol; and having a pH from about 5.5 to about 6.5. The fertilizer may contain nutrients and flavorants.

While it is only theory, the inventors have unexpectedly found that leaving a small amount of alcohol present in the fertilizer acts as a metabolic stimulant to the plants, increasing the ability of the plants to uptake any readily available nutrients, thereby increasing available nutrient content and encouraging growth and budding.

The alcoholic beverage used as the feedstock in the above method is typically a waste alcoholic beverage and may include but is not limited to wine, fortified wine, beer, distilled spirits, or mixtures of the same. The fortified wine may include but is not limited to brandy, grappa, port, sherry or mixtures of the same.

The alcohol content present in the alcoholic beverage is in the typical range for the specific type of beverage used as a feedstock. For example, the alcohol content in wine used as a feedstock can range from about 8% by volume to about 15% by volume. The alcohol content in fortified wine or distilled spirits used as a feedstock is higher.

In one embodiment of the invention, the minimum residual sugar content in the alcoholic beverages used as a feedstock is less than 1% w/v as glucose/sucrose. While it is theory, having a residual sugar content in this range is thought to have a positive effect on fertilizing vegetation In one embodiment, the base used to adjust the pH of the liquid is a strong base and may include potassium hydroxide, calcium hydroxide, magnesium hydroxide or mixtures of the same.

In one embodiment of the invention, the method includes the step of adding an additional nutrient to the liquid prior to its use as a fertilizer. The additional nutrient may include but is not limited to a source of nitrogen, a source of phosphorous, a source of potassium, a source of calcium, a source of magnesium, a source of sulfur, a source of copper, a source of iron, a source of manganese, a source of molybdenum, a source of zinc, a source of boron, or mixtures of the same. The nutrient may be added at any step in the method, including but not limited to after the distillation step, or after pH adjustment.

In one embodiment of the invention, the method includes the step of adding a flavorant to the liquid. The flavorant may include but is not limited to chocolate, peppermint, cinnamon, cherry, lemon, lime, orange, mandarin (tangerine), berry (strawberry, blackberry, cranberry, raspberry, blueberry, etc), banana, clove, licorice/anise, pear, apple, vanilla, olive, pumpkin, melon, pineapple, mango, grape, or mixtures of the same. The flavorant may be added at any step in the method, including but not limited to after the distillation step, or after pH adjustment.

In one embodiment, the invention embraces a method of producing a fertilizer from waste products generated from production of an alcoholic beverage, the method including the following steps: (a) distilling the waste alcoholic beverage to produce a liquid at the bottom of a still with an alcohol concentration of between about 0.005% by volume and 0.25% by volume; and (b) adjusting the pH of the liquid to a range of 5.5-6.5 using a base to produce a fertilizer.

In one embodiment, the invention is directed to a method of imparting flavor to a plant, the method including the following steps: (a) subjecting an alcoholic beverage or the waste product from production of an alcoholic beverage to distillation to produce a liquid at the bottom of a still with an alcohol concentration of between about 0.005% by volume and 0.25% by volume; (b) adjusting the pH of the liquid to a range of 5.5-6.5 using a base; (c) adding a flavorant to the liquid; and (d) fertilizing the plant by adding the flavored liquid to the soil surrounding the plant. The waste product from the production of an alcoholic beverage may include still bottoms, lees, fruit, skins, stems, seeds, yeast or mixtures of the same.

In one embodiment, the method of the invention may include the step of macerating the waste product prior to distillation. The waste product may include fruit, fruit skins, stems, seeds, or mixtures of the same.

The invention includes a solid or liquid/solid mixture agricultural foodstuff comprising a macerated by-product obtained from a waste stream from producing a fertilizer from an alcoholic beverage during the making of alcoholic beverages, said foodstuff comprising less than 7% sugar by volume and less than 2.5% ethanol by volume.

BRIEF DESCRIPTION OF THE DRAWINGS

FIGS. 1A, 1B, 1C and 1D are photographs of late stages of tomato plant growth (day 44).

DETAILED DESCRIPTION OF THE INVENTION

The present invention provides methods to produce natural fertilizer from fermented organic material and waste product derived from processing fermented organic material.

More specifically, the present invention provides methods for producing a liquid fertilizer from a feedstock that may include alcoholic beverages, waste product derived from the production of alcoholic beverages, or mixtures of the same. One step in the method of the invention is reducing the native alcohol content from fermented organic material and resultant fermented liquids in order to create a natural fertilizer for private and public agricultural use as described below.

In one embodiment, the method relates to producing a liquid fertilizer from discarded lees of wine and yeast. After wine production and pressing, the remaining portion of fruit skins, stems, seeds, yeast and wine remnant is collected. This waste material is typically discarded, e.g., taken to a landfill or tilled into a field for the next growing season. In the methods of the invention, the waste material (fruit skins, stems, seeds, yeast and wine remnant) may be macerated to the point where it becomes a liquid with minor particulate matter. The liquid may be filtered to remove at least a portion of the particulate matter. The liquid is then distilled to remove the majority of the volatile compounds and ethanol. Ethanol is potentially toxic to plants, even in moderate amounts, thus jeopardizing growth and viability. Excess ethanol is removed from the base liquid by distillation and may be captured to provide either industrial quality ethanol; or for permitted operators, the excess ethanol may be captured and concentrated according to a licensed distillation process. After distillation, the pH of the liquid is raised to a range from about 5.5 to about 6.5 using a base (e.g., potassium hydroxide, calcium hydroxide or magnesium hydroxide). Additional nutrients, such as soluble calcium and magnesium, can be added to the liquid.

In another embodiment, the method relates to producing a liquid fertilizer from a waste stream derived from the production of alcoholic beverages (e.g., still bottoms waste of brandy or other alcohol production, such as grain alcohol). After distillation to the desired alcohol content (e.g., in brandy production), waste is generated that may contain a residual ethanol content, albeit greatly reduced. Should the residual alcohol content in the waste stream be too high, a secondary distillation may be required to further reduce the proportion of alcohol. The need for this additional step would depend on the distillation method used, as methods of distillation can vary the residual alcohol content level. For example, distillation columns can remove a higher percentage of alcohol than a pot or alembic still, depending on the distiller's discretion. In a secondary distillation, excess ethanol is liberated from the base liquid, which may be captured to provide either industrial quality ethanol; or for permitted operators, the excess ethanol may be captured and concentrated according to a licensed distillation process. The pH of the liquid is then raised to a range from about 5.5 to about 6.5 using a base (e.g., potassium hydroxide, calcium hydroxide or magnesium hydroxide). Additional nutrients, such as soluble calcium and magnesium, can be added to the liquid.

In another embodiment, the method relates to producing a liquid fertilizer from waste fruit product (e.g., discarded or inedible fruit). Waste fruit product may be collected and fermented under controlled conditions with yeast (e.g., a *Saccharomyces* yeast species) to create a resultant ethanol rich mixture (just as in wine making) that may then be macerated into a liquid with fine particulate matter and distilled to remove ethanol. Excess ethanol is liberated from the base liquid, which may be captured to provide either industrial quality ethanol; or for permitted operators, the excess ethanol may be captured and concentrated according to a licensed distillation process. The pH of the liquid is then raised to a range from about 5.5 to about 6.5 using a base (e.g., potassium hydroxide, calcium hydroxide or magnesium hydroxide). Further nutrients such as soluble calcium and magnesium may be added.

In other embodiments, the process described above may be used to convert waste streams from the manufacture of beer (e.g., waste trub) into a useful liquid fertilizer.

The methods of the invention provide for the adjustment of pH level by the addition of a base to slightly raise pH to a nominal range of from about 5.5 to about 6.5. In one embodiment, the base added for pH adjustment is a strong base, which can include but is not limited to potassium hydroxide, magnesium hydroxide, and calcium hydroxide. The addition of a strong base to the acidic solution frees up cations such as potassium, calcium and magnesium, and is thought to have the effect of supplying additional beneficial compounds to the fertilizer that can readily be taken up into plants. Additional nutrients (e.g., solutions of soluble calcium and magnesium) may be added for plant uptake.

The methods of the invention may be applied to any fermented fruit substrate or macerated agglomeration (e.g., grape, apple, cherry, peach, and pear). Further, by maceration of residual post-fermentation waste (most notably from the production of wine products), the methods of the invention can return economic as well as agriculturally beneficial effects immediately, without having to undergo a natural decomposition process which can take multiple months and still require proper salt and electrolyte balancing so as to not to harm the root structure of the plants to which the fertilizer is applied.

Another embodiment of the present invention relates to the solid material which cannot be filtered following maceration. Such solid material may still be distilled to significantly reduce ethanol content. The solid material can then be pelletized or dehydrated and reconstituted into agricultural foodstuffs suitable for fish, bovine, swine, etc. . . . Because the residual sugar content is minimized through fermentation and ethanol removed through distillation (either pre- or post maceration), the foodstuffs exhibit broken down organic components having low sugar by volume content (less than 7% sugar by volume) that are more easily digestible by agricultural food stock, thus increasing dietary efficiency and reducing environmentally harmful solid and gaseous output and could be directly in line with the waste-stream produced foodstuff's ability to effect bacterial population colonization in the stomach/intestines of the animals or react differently with the current environment present within the animal's gastrointestinal tract. Byproducts from wine making are of particular interest. The resultant product, following maceration and/or dehydration, is a solid agricultural foodstuff comprising a macerated by-product obtained from a waste stream from producing a fertilizer from an alcoholic beverage during the making of alcoholic beverages, said foodstuff comprising less than 7% sugar by volume and less than 2.5% ethanol by volume. The material remaining after being subjected to distillation, maceration, and/or dehydration that cannot be used in liquid fertilizer can also be fortified with essential vitamins, minerals, and amino acids ideal to the feed's final livestock destination. Such vitamins may be, but are not limited to, vitamin A, B, C, D, E, K, and complexes thereof (for example thiamin (B1), niacin (B3), cobalamin (B12), folic acid, etc. . . . Such minerals may be, but are not limited to, calcium, magnesium, manganese, molybdenum, iron, copper, chromium, iodine, phosphorous, potassium, selenium, sodium chloride, and zinc. The final amount and combination of vitamins, minerals, and amino acids will vary based upon the animal's requirements and may be added separately at a later date. The material remaining after being subjected to distillation, maceration and/or dehydration that cannot be used in liquid fertilizer can also be fortified with essential vitamins, minerals, and amino acids ideal to the feed's final feedstock destination. Such vitamins may be, but are not limited to, vitamin A,B,C,D,E,K and complexes thereof (for example thiamin (B1), niacin (B3), cobalamin (B12), folic acid, etc.). Such minerals may be, but are not limited to, calcium, magnesium, manganese, molybdenum, iron, copper, chromium, iodine, phosphorus, potassium, selenium, sodium chloride, zinc. The final amount and combination of vitamins, minerals and amino acids will vary based on the animals requirements and may be added separately at a later date by the farmer should they choose to accept the feedstock that has been the result of the methods of the present invention.

The solid material can then be pelletized or dehydrated and reconstituted into agricultural foodstuffs suitable for fish, bovine, swine, etc. . . . Residual sugar content is minimized through fermentation and ethanol removed through distillation (either pre- or post maceration). As evident, an embodiment of the present invention relates to the solid material which cannot be filtered following maceration. The foodstuffs exhibit broken down organic components having low sugar by volume content (less than 7% sugar by volume) that are more easily digestible by agricultural food stock, thus increasing dietary efficiency and reducing environmentally harmful solid and gaseous output and could be directly in line with the waste-stream produced foodstuff's ability to effect bacterial population colonization in the stomach/intestines of the animals or react differently with the current environment present within the animal's gastrointestinal tract. Byproducts from wine making are of particular interest. The resultant product, following maceration and/or dehydration, is a solid agricultural foodstuff comprising a macerated by-product obtained from a waste stream from producing a fertilizer from an alcoholic beverage during the making of alcoholic beverages, said foodstuff comprising less than 7% sugar by volume and less than 2.5% ethanol by volume.

In summary, the invention relates to a foodstuff and a method of producing a solid or liquid and solid foodstuff suitable for fish, bovine, swine, and the like for increasing dietary efficiency and reducing environmentally harmful solid and gaseous output.

The methods of the invention are thought to eliminate any undesirable organic pest from macerated harvest waste, thus eliminating the need for disposing of certain products as a hazardous material or waste in certain wine growing regions. For example, the methods of the invention are thought to eliminate the possibility of viable Glassy-Winged Sharpshooter pests surviving into the resulting fertilizer products. Due to the heat applied during the distillation step, some breakdown of possible pesticides may also result.

The methods of the invention result in the production of an immediately useable, water-soluble fertilizer at a nominal pH level of 5.5 to 6.5 for direct application to any type of agricultural product without dilution. The fertilizer produced by the methods of the invention has shown in empirical testing to be at least as good as, and in some cases, far superior to, commercially available fertilizers. Current commercially available fertilizers of this type generally have extremely low (acidic) pH characteristics, which mandate significant dilution with water in order to reach a nominal 5.5 to 6.5 pH. This increases the cost and reduces the efficiency of their use.

The fertilizer produced by the methods of the invention have been shown through testing to be an organic pest deterrent and have repellent characteristics when applied as a fine mist over target agricultural plants.

In one embodiment, the invention also provides methods for imparting flavor to a plant starting with the feedstocks described above and subjecting the feedstock to further processing prior to fertilizing the plant. For example, certain organic flavorants, (e.g., chocolate, peppermint, cherry, cinnamon) may be added to the liquid fertilizers produced by the method of the invention. This differs from current commercial flavor enhancement of plant materials, which relies on the post-harvest addition of flavors, or on genetic modification and alteration of plant lines.

In one embodiment of the invention, the flavorant is in liquid form. For example, when chocolate is used as a flavorant, the chocolate has been liquefied or dissolved in a solvent.

The methods of the invention also encompass transmitting flavor to a plant through other means, including, for example, adding a flavorant to an existing commercial fertilizer. As in the method described above, this embodiment is not limited to the use of any particular flavorant. The fertilizer is then applied to the soil surrounding the plant, and the flavor is transmitted to the plant through the fertilizer.

The invention also relates to a method of producing both an alcoholic beverage (e.g., wine) and fertilizer.

Broadly speaking, wine, and henceforth fertilizer, may be produced from a variety of fruit, vegetable and grain-based substrates (e.g., apples, pears, cherries, plums) in addition to varietals of grape species. The process of wine making begins with a sugar-containing natural substrate (traditional grape wine making will be emphasized in this discussion). The fruit is harvested during a time in which sugar (or "Brix") content and acid content are favorable for yeast fermentation. For example, in grape-based wine, fructose and glucose are present in near equal amounts, and acidity is present within a range that will promote yeast fermentation while discouraging spoilage and enhancing certain flavors in the final wine product. Individual acid levels as well as overall acidity, or pH of the grape, may be measured and aid in determining the time for harvest as well as tangible factors like aroma, texture, color and environmental risk. These qualities will vary somewhat as the type of acids present differs depending on the fruit, vegetable or grain used. For example, malic acid is the predominant acid in grapes, pears, and cherries, whereas citric acid is the predominant acid present in oranges, lemons and limes. Thus, each fruit has different properties during fermentation.

Once harvested, the fruit (e.g., grapes) is prepared for fermentation. More specifically, the fruit is typically destemmed, pitted (in some cases), and crushed. The resulting "must" or juice will begin fermentation with wild yeast present in the air within the first day, although commercially harvested yeast can be added to increase fermentation rate, alcohol content, and yield more predictable outcomes for the final product. Sugar and alcohol content are monitored until desired levels are reached and fermentation halted, or until most or all residual sugar is absent.

The resultant fermented juice may be separated from the solid components (pomace and future lees) through pressing. The liquid may then be distilled to remove the ethanol and further processed for use as a liquid fertilizer. The lees may be placed aside for distillation, maceration, filtration, and semi-solid fertilizer production. Otherwise, the fermented liquid and solids may be distilled together to remove the ethanol, then macerated and filtered to produce liquid fertilizer that includes particulate matter. The ethanol content in the final fertilizer product should be maintained to about 1% maximum by volume, preferably from 0.005% to 0.25% by volume.

Once distillation is complete (removal of the ethanol to a level between about 0.005% by volume and 0.25% by volume), flavors may be added to any of the above fertilizers. The additional mineral additives (such as calcium, magnesium, sodium) also may be added to the fertilizer. These steps may occur before or after neutralization with a strong base to a pH of 5.5 to 6.5. with a strong base liquid (such as potassium hydroxide) and bottled, or bottled at the resultant pH post distillation and mineral/flavor addition and a separate pre-determined vessel with the strong base attached to be added to the fertilizer when opened for optimal balancing to pH of 5.5 to 6.5.

The ethanol that is collected may be used for consumption under proper licensing or distributed for industrial uses.

In one embodiment, the invention provides for methods to produce (1) wine and (2) a fertilizer from waste products generated in the production of wine. The method comprises (a) processing grapes to prepare a must and pomace; (b) fermenting the must to produce wine; (c) separating the must from the pomace; (d) macerating the pomace to prepare a liquid with an alcohol concentration between 3% and 20% by volume; (e) subjecting the macerated pomace and waste must to distillation to produce a liquid at the bottom of a still with an alcohol concentration of between about 0.005% by volume and 0.25% by volume; and (f) adjusting the pH of the liquid to a range of 5.5 to 6.5 using a base to produce a fertilizer.

In one embodiment, the alcohol concentration of the liquid in step (d) of the above method is between 3% and 20% by volume. In another embodiment, the alcohol concentration of the liquid in step (d) is between 8% and 15% by volume. In a further embodiment, the alcohol concentration of the liquid in step (d) is between 10% and 12% by volume.

The examples herein are meant for illustrative purposes and are not intended to limit the scope of the invention.

Example 1: Testing the Effectiveness of the Fertilizer of the Invention on Growth of Tomato Plants Three pots were planted with four each of Glacier Red Tomato seeds according to seed packet directions. All plants were started with Miracle Grow organic potting soil and subjected to 12 hours of daylight in a simulated indoor growing environment. The initial pH of soil was 6.9. All plants were maintained at a temperature of 65 to 72° F.

The water only plant (Plant #1) was fed with water (pH 6.8) every two (2) days and subjected to 12 hours of sunlight each day. Plant #2 received the fertilizer produced by the methods of the invention (pH 5.9) every two (2) days and subjected to 12 hours of sunlight each day. Red burgundy wine was used as the feedstock for producing the fertilizer according to the method of the invention. Plant #3 was given a guano-based fertilizer (pH 3.2) every two (2) days that was diluted with water per provided instructions (1 tablespoon per 1 gallon of water for heavy feeding) and provided 12 hours of sunlight per day.

Figure 1A:
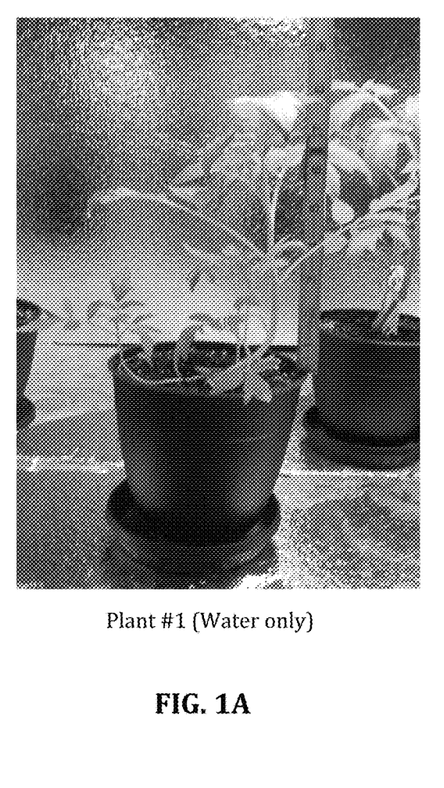
FIG. 1A is a photograph of tomato plant #1 treated with water only.
Figure 1B:
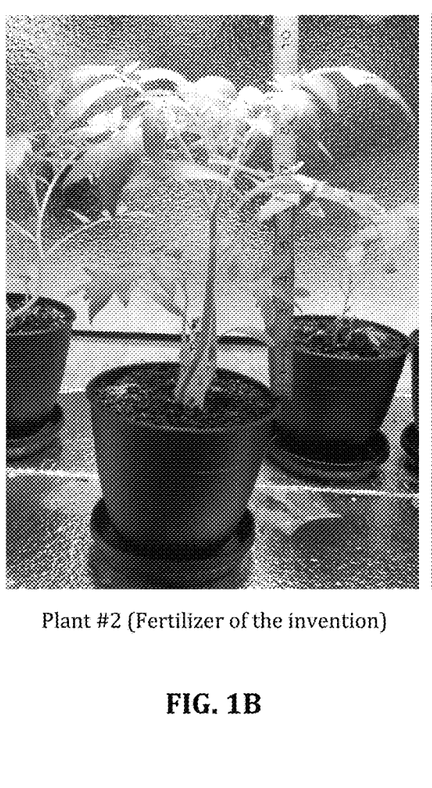
FIG. 1B is a photograph of tomato plant #2 treated with fertilizer produced by the methods of the invention showing increase in growth.
Figure 1C:
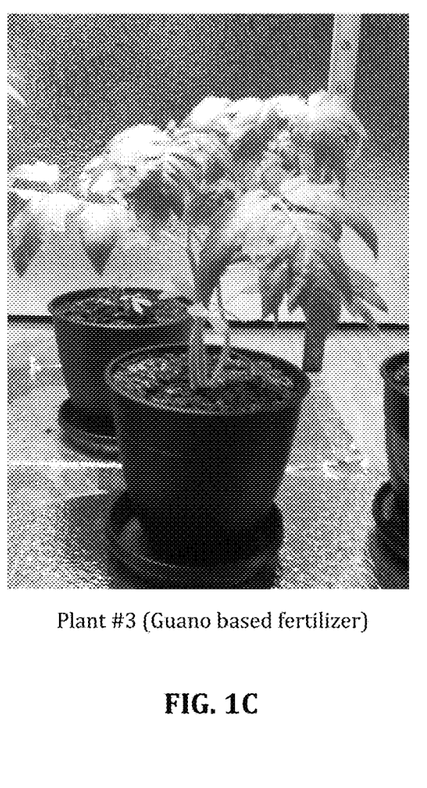
FIG. 1C is a photograph of tomato plant #3 treated with guano-based fertilizer.
Figure 1D:
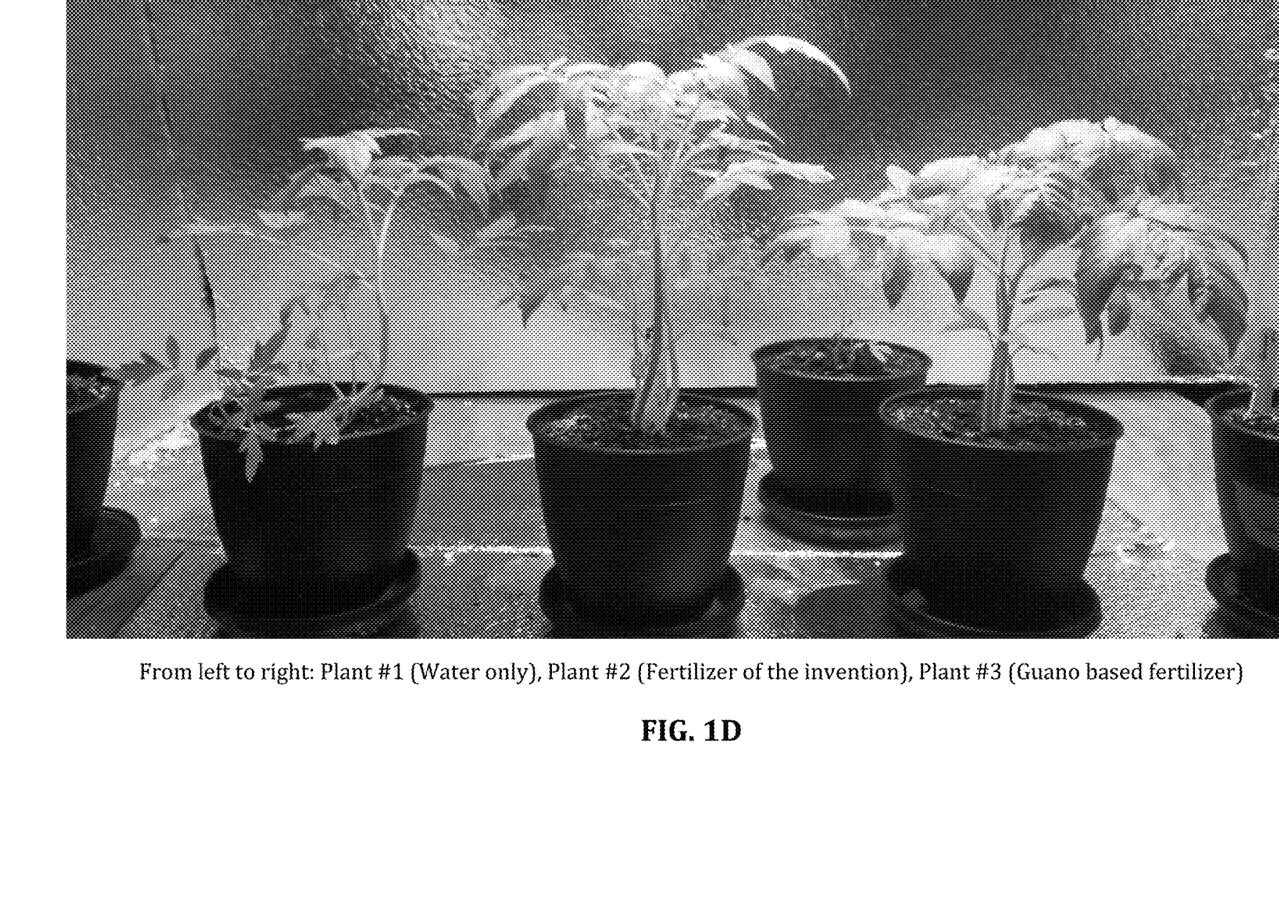
FIG. 1D is a photograph of, from left to right, tomato plant #1 treated with water only, plant #2 treated with fertilizer produced by the methods of the invention and plant #3 treated with guano-based fertilizer showing increase in growth in tomato plant treated with fertilizer of the invention.

After 44 days of growth in the indoor environment, Plant #1 had all three seedlings sprout with low growth from two seedlings (less than 3 inches) but had vertical growth of one seedling with a height of 7.75 inches (FIG. 1A). Plant #2 had all three seedlings sprout with all three reaching a height of over 9 inches with the largest being 9.5 inches (FIG. 1B). Plant #3 had all three seedlings sprout with all three reaching heights over six (6) inches with the largest being 7.75 inches (FIG. 1C). Tomato plants treated with fertilizer made using the method of the invention produced higher plant height compare to plants treated with water or guano-based fertilizer (FIG. 1D). A noticeable difference in quantity of growth is also observed between Plant #1 and the other two plants (FIG. 1D).

Example 2: Effect of the Fertilizer of Invention on Tomato Plants

Three pots were planted with four each of Glacier Red Tomato seeds according to seed packet directions. All plants were started with Miracle Grow organic potting soil and subjected to 12 hours of daylight in a simulated indoor growing environment. Initial pH of soil was 6.9. All plants were maintained at a temperature range of 65-72° F.

The water only plant (Plant #1) was fed with water (pH 6.8) every two days and subjected to 12 hours of sunlight each day. Plant #2 received the fertilizer produced by the method of the invention (pH 5.9) every two days and was subjected to 12 hours of sunlight each day. Plant #3 was given a guano-based fertilizer (pH 3.2) every two days that was diluted with water per provided instructions (1 tablespoon per 1 gallon of water for heavy feeding) and provided with 12 hours of sunlight per day.

Figure 2A:
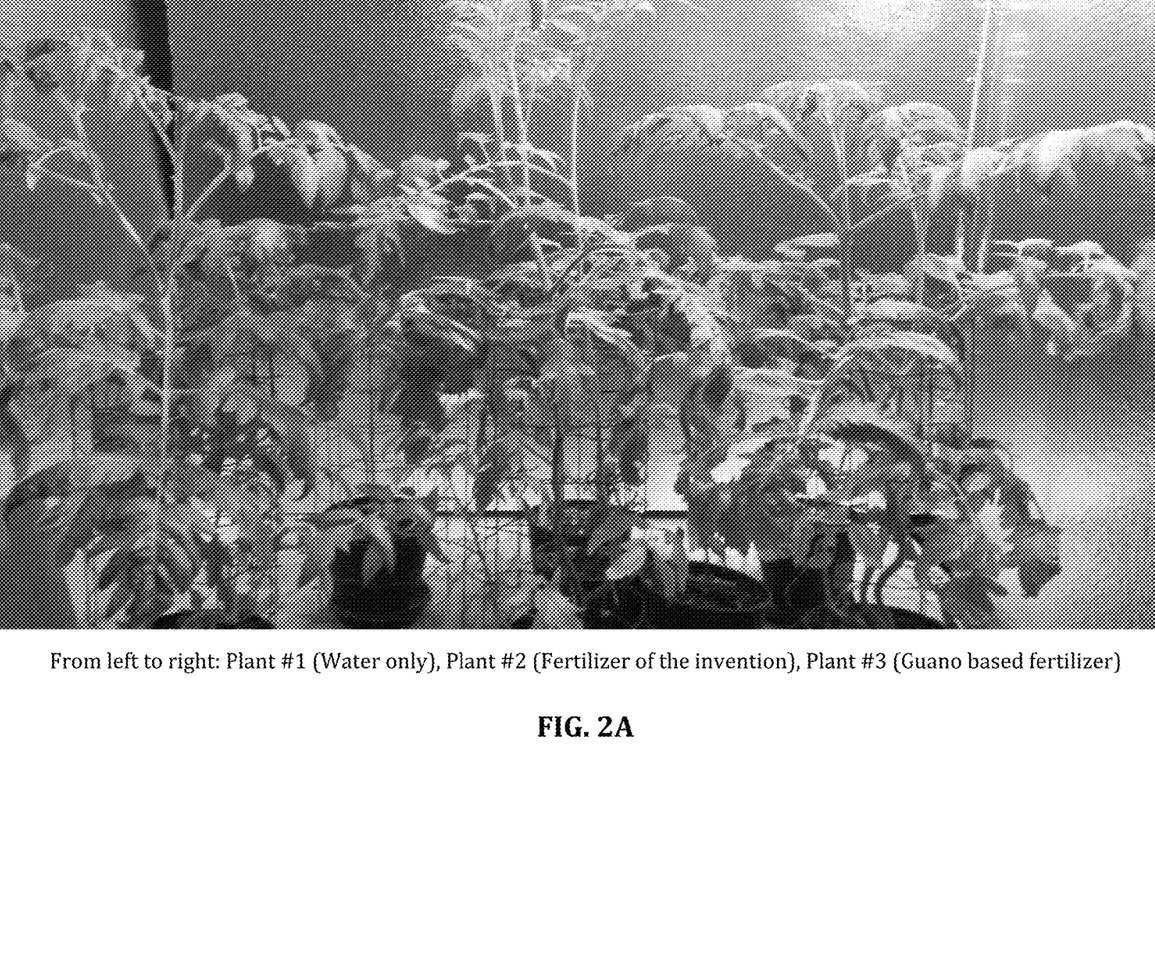
FIG. 2A is a photograph of, from left to right, tomato plant #1 treated with water only, plant #2 treated with fertilizer produced by the methods of the invention and plant #3 treated with guano-based fertilizer, showing increase in growth in tomato plant treated with fertilizer of the invention.

After 44 days of growth in the indoor environment, tomato plant #2 treated with the fertilizer of the invention had higher vertical growth when compared to tomato plant #1 treated with water and tomato plant #3 treated with guano-based fertilizer (FIG. 2A). In addition, after 44 days growth, flower buds appeared on tomato plant #2, which was treated with the fertilizer made using the methods of the present invention. No flower buds appeared on the tomato plants treated with water (#1) and guano-based fertilizer (#3).

Figure 3A:
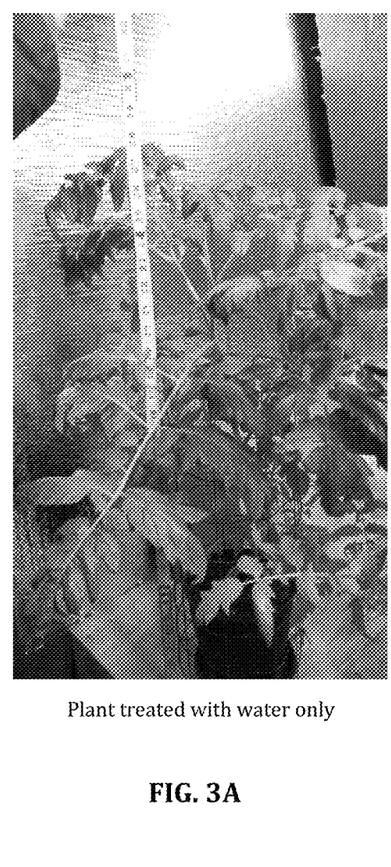
FIG. 3A is a photograph of tomato plant treated with water only showing a growth of 28 inches.
Figure 3B:
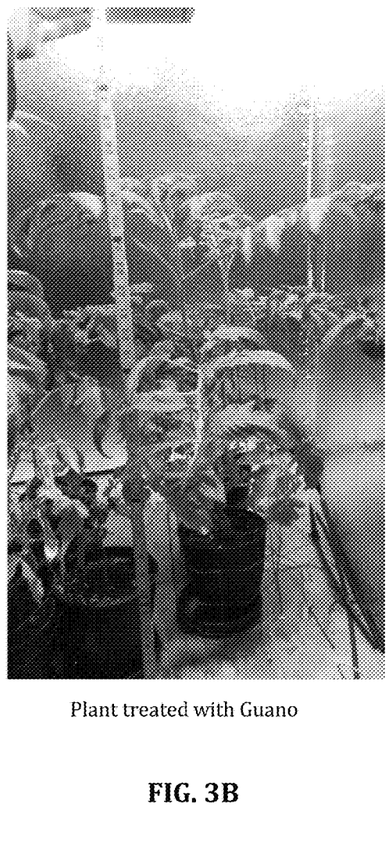
FIG. 3B is a photograph of tomato plant treated with guano-based fertilizer showing a growth of 27 inches.
Figure 3C:
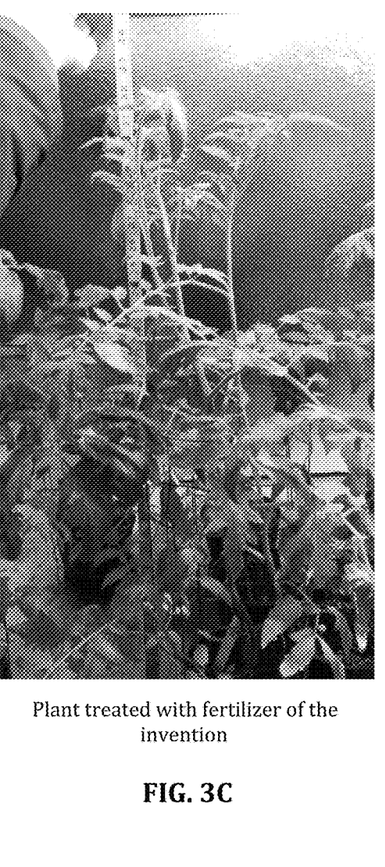
FIG. 3C is a photograph of tomato plant treated with fertilizer produced by the methods of the invention showing a growth of 32 inches.

Tomato plant #1 treated with water only had vertical growth of 28 inches (FIG. 3A). Tomato plant #3 treated with guano-based fertilizer showed a growth of 27 inches in height (FIG. 3B). Tomato plant #2 treated with fertilizer of the invention had a vertical growth of 32 inches.

Figure 2B:
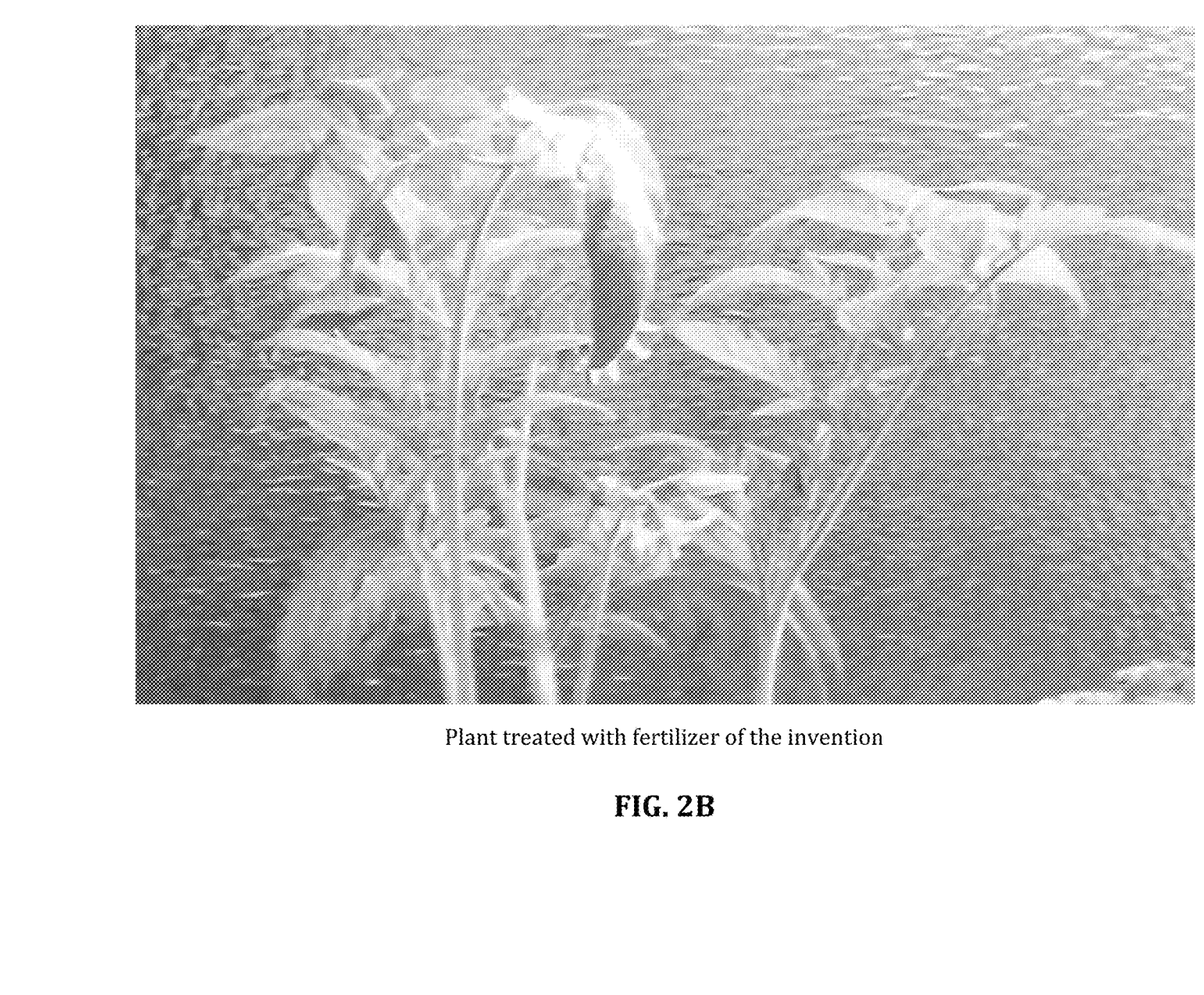
FIG. 2B is a photograph of tomato plant treated with fertilizer produced by the methods of the invention, showing the plant was first to produce flowers.
Figure 4A:
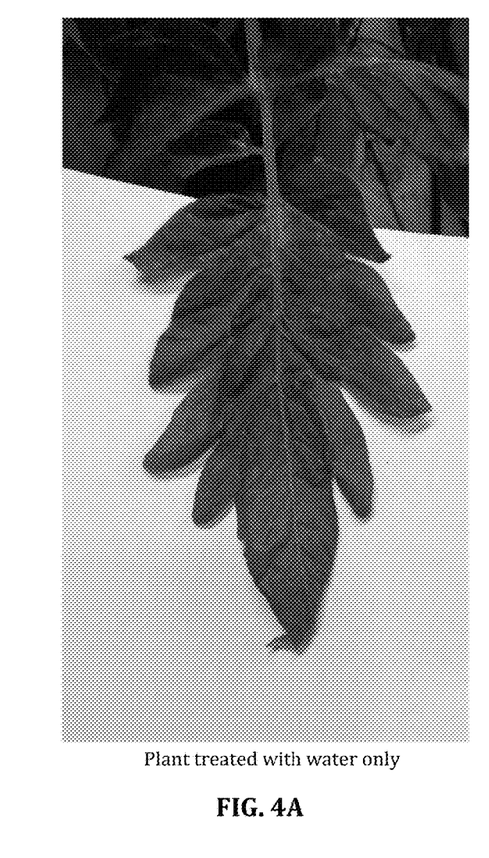
FIGS. 4A and 4B are photographs of leaves of tomato plants treated with water only (FIG. 4A) and fertilizer produced by the methods of the invention (FIG. 4B), showing healthier leaf in the tomato plant treated with the fertilizer of the invention.
Figure 4B:
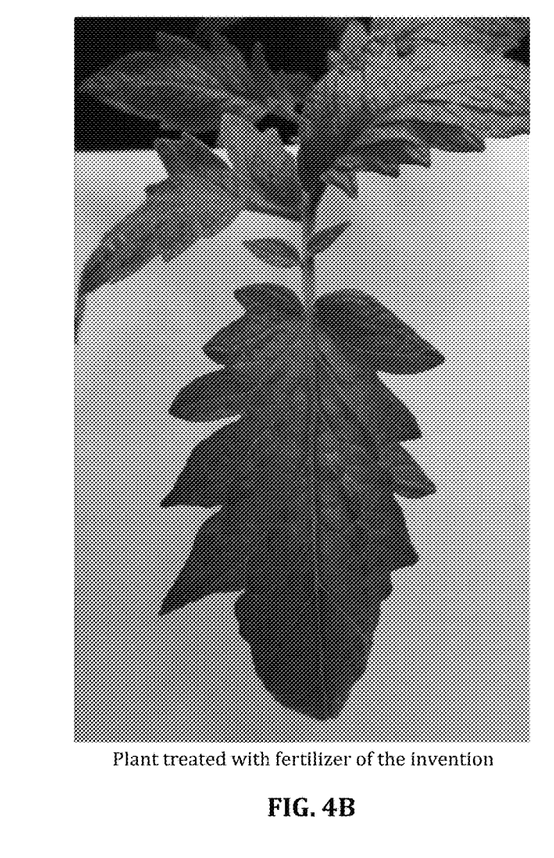
Figure 5A:
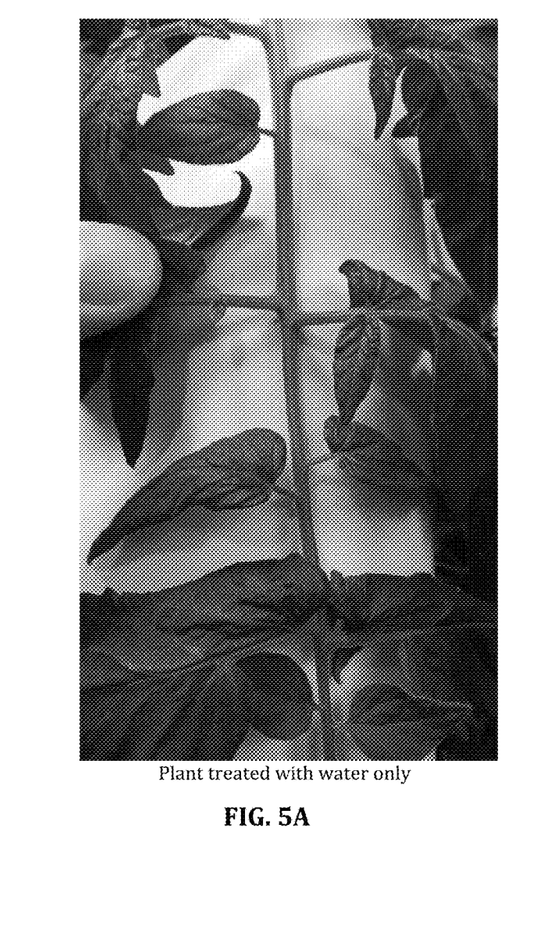
FIGS. 5A and 5B are photographs of stems of tomato plants treated with water only (FIG. 5A) and fertilizer produced by the methods of the invention (FIG. 5B), showing a healthier stem in the tomato plant treated with the fertilizer of the invention.
Figure 5B:
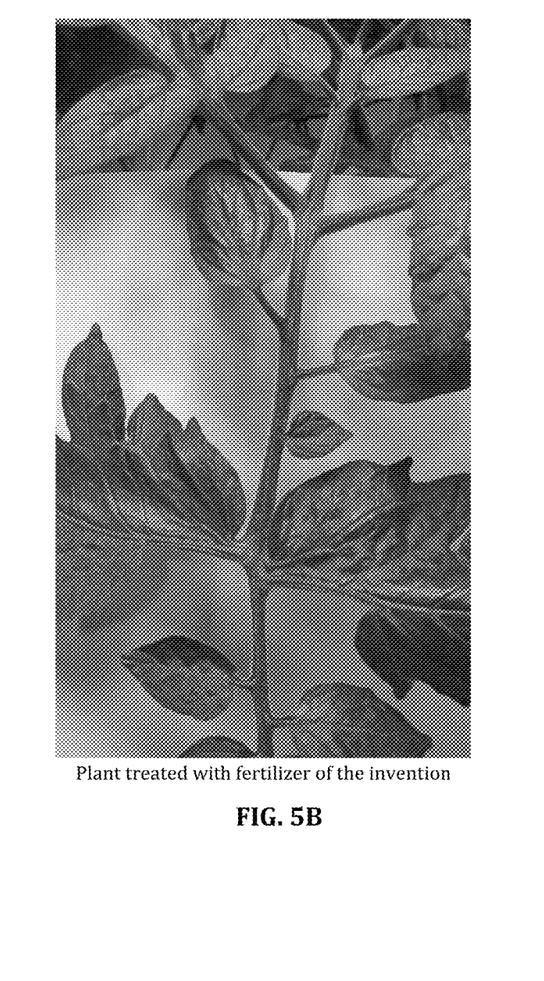
Figure 6A:
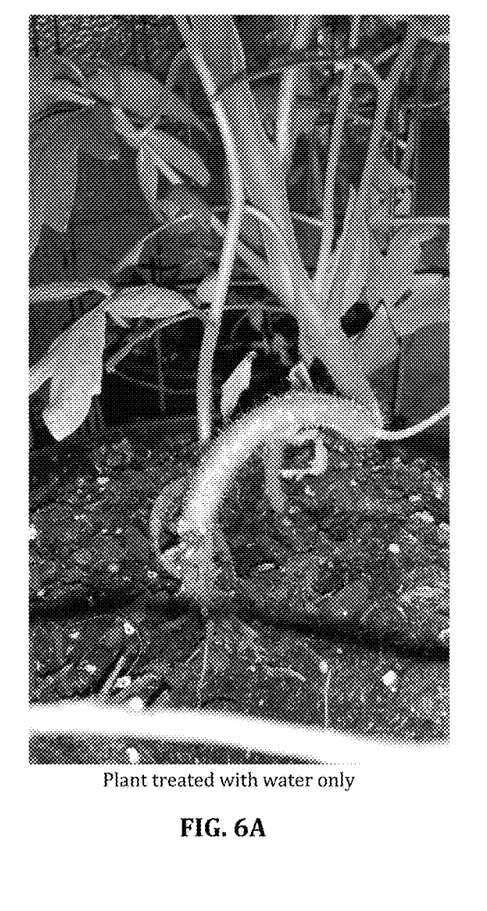
FIGS. 6A and 6B are photographs of stems of tomato plants treated with water only (FIG. 6A) and fertilizer produced by the methods of the invention (FIG. 6B), showing a more rigid, colorful and healthier stem in the tomato plant treated with the fertilizer of the invention. The tomato plant treated with the fertilizer produced by the methods of the invention also had a more potent tomato plant smell.
Figure 6B:
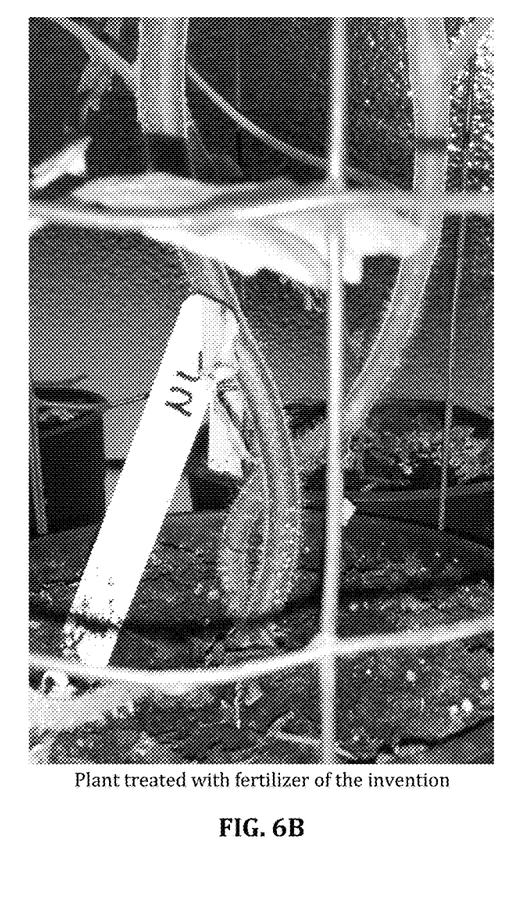

Tomato plant #2, treated with fertilizer made using the method of the present invention, was the first plant to produce flowers (FIG. 2B). Tomato plant #3, treated with the guano-based fertilizer, produced flowers 33 days after tomato plant #2, with approximately half the amount of flowers present. Plant #1 has not produced any flowers even after 110 days, although four potential buds were present. The leaves of plant #2 were healthier when compared to the leaves of plant #1 treated with water only (FIGS. 4B and 4B).

The stems of tomato plants treated with the fertilizer made using the method of the invention were more rigid, colorful and healthier than the stems of tomato plants treated with water only (FIGS. 5A, 5B, 6A and 6B). Further, the tomato plant treated with the fertilizer of the invention had a more potent tomato plant smell.

After 95 days, the tomato plants were transplanted to larger containers as they exceeded the sprouting container. More specifically, the plants were moved from their 0.5 gallon sprouting containers to four gallon pots, once again using Miracle Grow organic soil as the medium. The root ball for the three tomato plants showed a significant difference. Tomato plant #1 treated with water only had minimal root ball and was loose and fragile. Tomato plant #3 treated with guano-based fertilizer showed a more significant root ball. It was a bit tighter and slightly more robust than the root ball of tomato plant #1. Tomato plant #2 treated with fertilizer made using the method of the invention exhibited a completely root-bound and tight root ball with no more room for it to expand in the container.

After four months into the growth observation of the tomato plants, the plants were repotted into 2.5 gallon containers and continued to be fed each type of their designated individual fertilizers (guano based, waste-stream produced fertilizer invention, and water). After three months in 2.5 gallon containers, (seven months total growing time) the plants were moved to seven gallon containers and given four ft. cages to allow further growth and flowering in open environment with identical positioning to one another, thus maintaining equal light exposure, temperature, and environmental conditions.

Root ball formation was noted during the transplant to the seven gallon containers. The tomato plant that was fed water only showed loose root formation in the lower $2/3^{rd}$ portion with loose topsoil. The guano based fertilizer plant showed tighter and more pronounced root ball formation in the lower $2/3^{rd}$ portion, but also exhibited loose topsoil. The waste stream fertilizer showed dense root formation with root extensions throughout all levels of the soil and exhibited minimal unincorporated topsoil.

Fruit formation of the guano based fertilizer plants and the waste stream fertilized plants showed roughly equal fruit yield during the summer, but the waste stream fertilized plant continued to produce fruit several weeks beyond the guano based fertilizer plant. The water fed control plants produced less fruit and for less time overall than both fertilizers.

Example 3: Flavor Transmission to Plants

Flavor transmission was confirmed via medical marijuana (cannabis) samples with a double blind study that introduced three samples from similar species of plants and presented them for both a smell as well as a vaporization test. The panel consisted of three medical marijuana users who were not privy to any information about the samples prior to exposure. Three samples were presented in a side-by-side comparison. Sample 1 (labeled numerically and identity known only to the inventors) was obtained from a plant treated with fertilizer made by the methods of the invention, the fertilizer including mild hints of peppermint in the final mixture. Sample 2 was obtained from a plant that was treated with fertilizer made by the method of the invention, the fertilizer having been infused with 100% cacao dark chocolate (fair trade). Sample 3 was obtained from a plant treated with a bat guano/worm casing fertilizer. Participants were asked not to speak during the trial so as not to influence one another's judgment. The following results were obtained.

Smell:

All three participants identified a significant and very apparent different aroma for Sample 2 on initial smell compared to either of the other two samples. Participants varied on description of potential scents ranging from "earthy" to "brewed coffee". Both Sample 1 and Sample 3 contained roughly similar indistinguishable notes.

Taste Through Vaporization:

Sample 1 was described by all participants as having just a mild hint of peppermint along with citrus/fruit flavors. All three participants identified Sample 2 as having significant "smooth coffee and chocolate flavors." Sample 3 was not remarkable for any significant flavor distinguishable from what the participants noted as "usual cannabis" and "tasted how I expected it to."

While it is theory, it must be noted that vaporization is thought to reduce the flavor in cannabis Samples 1 and 2 prior to sensory perception by the participants. This is thought to be due to volatilization of any transmitted flavorant compounds.

Example 4: Flavor Transmission to Plants (Test 2)

Three test subjects agreed to undertake a round of blind taste testing to determine flavor transmission among cannabis plants fertilized with the fertilizer made by the methods of the present invention. Similar to the previous test, all participants were medical marijuana users and unaware of the samples' identity and knew nothing of additional flavors potentially being added or present in the fertilization of the experimental plants. Unlike the previous test, the participants smoked each version of the products once it had been rolled using generic paper used to create each participant's own smoking apparatus.

Example 5: Lettuce Experiment Results: Growth

To test further root ball formation and flavor transmission by the invention, four planter boxes (8" by 30") were planted with Dark Green Lettuce seeds per the manufacturer's instruction, in stock Miracle Grow Organic Soil in an outdoor environment side by side with equal light and environmental exposure. Box #1 was watered with water only on a regular watering schedule per the seed supplier instruction. Box #2, 3, and 4 were watered with cherry, chocolate, and peppermint fertilizers. The amount of fertilizer and water applied to the plants was measured during each watering event which occurred at similar time of day for each watering event and in equal amounts of liquid to which the water only plant received.

Plants were extracted at 8 weeks from the planting boxes and stem girth and root ball formation were measured. All waste stream fertilized plants exhibited similar size and two random samples were selected from fertilized plants and from water only plants to be photographed and measured.

The plants fertilized with the waste stream fertilizer invention showed significantly larger and more extensive root formation than the water only plants. Height was not included in the measurements as the convolutions of the stems distorted proportions but overall length of the fertilized stems were 4.3 inches longer than the water only plants and had an average of 4-6 leaves more than the water only plants. Girth of the stems was measured on average 3.5 inches up from the soil level but measurements were taken at the thickest portion of the stem. The plant stems fertilized with the invention were 1.5 mm thicker on average than the water only plants.

Lettuce Experiment Results: Taste

After 8 weeks, the plants were harvested, leaves washed thoroughly and labeled and a blind taste test with 4 individuals was held. The participants were not aware of any flavor being added to the fertilizer only that they were there to evaluate flavor of the lettuce samples and recall any specific differences that existed between the samples. Samples were labeled #1, 2, 3, and 4 and the four individuals were asked to write their taste experience after sampling a leaf from each sample.

Sample #1 (water only) had no noted differences between the participants only that "tasted like lettuce". Sample #2 (fertilizer invention with cherry flavors) was noted by 2 examiners as having a more vibrant, slightly sweet flavor compared to the first sample, and the other 2 examiners noting distinct positive flavor differences with the first sample. Sample #3 (fertilizer invention with chocolate flavors) was recognized by all four individuals as having a much more mellow, earthy flavor than they had expected and much less astringent characteristics than they felt lettuce normally has. Sample #4 (fertilizer invention with peppermint) was noted by all four examiners as having a more herbal flavor than "normal" lettuce with one examiner identifying "there's like notes of wintergreen or mint or something there".

Experiment 6: Cannabis Grower Results from Northern CA

A grower in a smaller sanctioned medical growing facility in Northern California began using our fertilizer the prior growing season to test on several of his plants. After seeing the results the previous year, he agreed to participate in the second phase of testing. He grew "Big Bud" variety of Indica Cannabis only. His facility has both an indoor and outdoor growing areas. He was provided several different variants of the fertilizer invention (pear berry, cherry, chocolate, and peppermint). His plants were fed on a regular basis with half his crop receiving his "normal" combination of fertilizer and half his crop received our waste stream fertilizer invention. After half the season of mediocre growth with his "normal" fertilizer and superior growth noted with our fertilizer, he switched almost his entire crop to our waste stream fertilizer for the last 6 to 8 weeks before harvest.

Plants that had been fed the growers "normal" fertilizer never achieved the same height or bud formation of those fed the waste stream fertilizer invention from the beginning. The grower noted a "significant increase in growth from what I expected". He stated "the yield from the crop this year was more than I am used to both indoor and outdoor, and the possibility of unique flavor being imparted onto it helps me to differentiate the crop from other growers."

Samples from this grower's crop were used for the taste tests noted in the present application that have been conducted. The grower changed from a "Banana Kush" strain in the previous year to the "Big Bud" strain for the above mentioned test due to personal preference.

Experiment 7: Cannabis Grower Results from Willow Creek, Calif.

A grower in a large, sanctioned medical marijuana growing facility in Northern California began using our waste stream fertilizer (samples of both a peppermint and regular variety) exclusively on several of his outdoor plants from seedlings to harvest, following an identical fertilizer and water schedule that he applied to his normal plants (all of Indica variety) in identical burlap pots with stock soil. At week 6, he noted similar growth of the test plants compared with his normal crop with a minor increase in height of the fertilizer test plants compared to his normal plants (measured average of 4 inches above his standard plants). At week 10, he recorded a "noticeable" increased in height of the test plants compared to his normal crop (12 inches). At week 14, he asked us to visit the site to see the significant increase in growth of the waste stream fertilized plants over his normal crop, an 18 to 20 inch difference from his normal crop.

The grower was aware of the potential for possible flavor/scent being incorporated into the waste stream fertilizer, but was unaware of what flavor or which fertilizer sample may contain it. He noted that one of the specific plants carried a "noticeable minty scent" when touched. Once we returned home from the site visit, we confirmed to ourselves only, by unique fertilizer sample number supplied, that it was indeed being fed the waste stream fertilizer that contained peppermint flavors. The grower was never made aware of such information until after the harvest.

Experiment 8: Flavor Transmission to Plants: Taste Testing of $2^{nd}$ Crop of "Flavored" Cannabis Flavor transmission was once again confirmed in a test with four medical cannabis users that were not aware of previous testing sessions. This study was a single blind study as the examiner had some knowledge of the identity of possible flavor transmission. Three samples were tested, but all participants were unaware of flavor composition. A baseline was established with Sample #1 being taken from a plant fertilized with our Northern California growers normal fertilizer concoction of a guano based fertilizer in a stock soil (variety of "Big Bud" species of Indica cannabis). Sample #2 was a chocolate based fertilizer infused with 100% cacao dark chocolate (fair trade). Sample #3 was a mixed Pear/Berry fertilizer that had been infused with the extracts of certain fruit creating fragrant fruit essences within the fertilizer.

The results are set forth below.

Smell—

Sample #1 was once again unremarkable with 3 of the 4 participants noting nothing in particular other than light astringent scent with "normal smell". Sample #2 was quoted by all participants as having a strong scents described as "like the notable smell of the first rain on dry soil" and "less than subtle earth tones that remind you of coffee beans". Sample #3 was likened to "a very light tea that had some slight fruit or sweet herb notes" but otherwise unremarkable.

Taste—

Through burning in conventional cannabis apparatus: Sample #1 was described by most of the participants as having a traditional flavor. Sample #2 received comments of "heavy earthy notes like coffee" by 3 of the 4 participants. Sample #3 was said to be "Sweeter than I expected", and containing fruit notes "like the sweet scents from a bouquet of flowers" with notes of apple by two of the participants and a "more sweet potpourri flavor" compared to the first sample.

Experiment 9: Golf Course Use of Fertilizer of the Invention

To further test the effectiveness of the fertilizer of the invention on plant life, a contact within the Greenkeeper Staff (Head Greenskeeper) for a private golf course in the Southern California region was asked if he would experiment with the invention on a part of his course. Since his staff did not need to concern themselves to any complicated mixing regimen or hazardous exposure due to the natural contents of the waste stream fertilizer invention, the experiment was authorized to proceed. The Greenkeeper marked off a 1000 square foot section of the rough that had trouble in the past with being able to fill in and proceeded with a regular watering schedule with our fertilizer.

Following four weeks of regular use with the fertilizer of the invention, the Head Greenkeeper observed an obvious change in area that had been receiving treatment compared to the adjacent untreated area. The Greenkeeper staff continued applications and trimming as normal.

After eight weeks, we were invited for a site visit and noted significant increase in depth of coloration of the area as well as lateral fill in areas that were once barren.

After twelve weeks, the Head Greenkeeper sent final photographs that indicated almost full coverage in the once previous barren areas and, in his opinion, an overall increase in health of the grass in the area that was treated with the fertilizer invention was achieved.

As the present invention may be embodied in several forms without departing from the spirit or essential characteristics thereof, it will be understood that the invention is not limited by the details of the foregoing description, unless otherwise specified, but rather should be construed broadly within its spirit and scope as defined in the appended claims, and therefore all changes and modifications that fall within the metes and bounds of the claims. Accordingly, the invention is defined by the appended claims wherein:

What is claimed is:

1. A method of producing a fertilizer from an alcoholic beverage, the method comprising:
    (a) subjecting the alcoholic beverage to distillation to produce a liquid at the bottom of a still with an alcohol concentration of between about 0.005% by volume and 0.25% by volume; and
    (b) adjusting the pH of the liquid to a range of 5.5 to 6.5 using a base to produce a fertilizer.

2. The method of claim 1, wherein said alcohol concentration is between 0.05% by volume and 0.25% by volume.

3. The method of claim 1, wherein the alcoholic beverage produced by fermentation is selected from the group consisting of wine, fortified wine, beer, distilled spirits and mixtures of the same.

4. The method of claim 3, wherein the fortified wine is a member of the group consisting of brandy, grappa, port, sherry and mixtures of the same.

5. The method of claim 1, wherein the base is a member selected from the group consisting of potassium hydroxide, calcium hydroxide, magnesium hydroxide, and mixtures of the same.

6. The method of claim 1 further comprising the step of adding a nutrient.

7. The method of claim 6, wherein the nutrient comprises a source of nitrogen, a source of phosphorous, a source of potassium, a source of calcium, a source of magnesium, a source of sulfur, a source of copper, a source of iron, a source of manganese, a source of molybdenum, a source of zinc, a source of boron, or mixtures of the same.

8. The method of claim 1 further comprising the step of adding a flavorant to the liquid.

9. The method of claim 8, wherein the flavorant is chocolate, peppermint, cherry, cinnamon or mixtures of the same.

10. A method of imparting flavor to a plant, the method comprising:
   (a) subjecting an alcoholic beverage, waste product from the production of an alcoholic beverage, or mixtures of the same to distillation to produce a liquid at the bottom of a still, said liquid having an alcohol concentration of between about 0.005% by volume and 0.25% by volume;
   (b) adjusting the pH of the liquid to a range of 5.5 to 6.5 using a base;
   (c) adding a flavorant to the liquid; and
   (d) fertilizing the plant by adding the flavored liquid to the soil surrounding the plant.

11. The method of claim 10, wherein the flavorant is chocolate, peppermint, cherry, cinnamon or mixtures of the same.

12. The method of claim 10, wherein the alcoholic beverage is wine or a fortified wine.

13. The method of claim 10, wherein the waste product from the production of an alcoholic beverage comprises still bottoms, lees, fruit, skins, stems, seeds, yeast or mixtures of the same.

14. The method of claim 10, further comprising the step of macerating the waste product prior to distillation.

15. A method of producing a fertilizer from waste products generated in the production of wine, the method comprising:
   (a) processing grapes to prepare for fermentation;
   (b) fermenting the processed grapes to produce wine;
   (c) collecting a waste stream generated as a byproduct from steps (a) and (b), said waste stream comprising pomace and having an alcohol concentration of between 3% and 20% by volume;
   (d) macerating the waste stream;
   (e) distilling the waste stream to produce a liquid at the bottom of a still having an alcohol concentration between about 0.005% by volume and 0.25% by volume; and
   (f) adjusting the pH of the liquid to a range of 5.5 to 6.5 using a base to produce a fertilizer.

16. The method of claim 15, wherein the fertilizer is a liquid.

17. The method of claim 15, wherein the waste stream has an alcohol concentration between 3% and 20% by volume.

18. A plant fertilizer comprising a waste product from the production of an alcoholic beverage, said waste product having an alcohol concentration of about 0.005% by volume of said waste product to about 0.25% by volume of said waste product, and a pH from about 5.5 to about 6.5.

19. The plant fertilizer of claim 18, wherein said waste product from the production of said alcoholic beverage is from a member selected from the group consisting of still bottoms, lees, fruit, skins, stems, seeds, yeast, and mixtures of the same.

20. The plant fertilizer of claim 18, wherein said alcoholic beverage is a member selected from the group consisting of wine, fortified wine, beer, distilled spirits, and mixtures of the same.

21. The plant fertilizer of claim 20, wherein said fortified wine is a member selected from the group consisting of brandy, grappa, port, sherry, and mixtures of the same.

22. The plant fertilizer of claim 18, wherein said fertilizer contains a flavorant.

23. The plant fertilizer of claim 22, wherein said flavorant is a member of the group consisting of chocolate, peppermint, cherry, cinnamon, and mixtures of the same.

24. The plant fertilizer of claim 18, wherein said fertilizer contains a nutrient.

25. The plant fertilizer of claim 24, wherein said nutrient is a member of the group consisting of a source of nitrogen, a source of phosphorous, a source of potassium, a source of calcium, a source of magnesium, a source of sulfur, a source of copper, a source of iron, a source of manganese, a source of molybdenum, a source of zinc, a source of boron, and mixtures of the same.

26. The plant fertilizer of claim 18, wherein said ethanol is present from 0.005% by volume to 0.25% by volume.

* * * * *